US00PP25378P3

(12) United States Plant Patent
Leelaspibl

(10) Patent No.: US PP25,378 P3
(45) Date of Patent: Mar. 24, 2015

(54) ***ASPIDISTRA* PLANT NAMED 'LEELASPIBL'**

(50) Latin Name: *Aspidistra elatior*
Varietal Denomination: LEELASPIBL

(71) Applicant: Anong Leelaspibl, Bangkok (TH)

(72) Inventor: Anong Leelaspibl, Bangkok (TH)

( * ) Notice: Subject to any disclaimer, the term of this patent is extended or adjusted under 35 U.S.C. 154(b) by 35 days.

(21) Appl. No.: 13/986,395

(22) Filed: Apr. 26, 2013

(65) Prior Publication Data

US 2014/0325721 P1 Oct. 30, 2014

(51) Int. Cl.
*A01H 5/00* (2006.01)

(52) U.S. Cl.
USPC ..... Plt./373

(58) Field of Classification Search
CPC ..... A01H 5/00
USPC ..... Plt./263.1, 373
See application file for complete search history.

*Primary Examiner* — June Hwu
*Assistant Examiner* — Keith Robinson

(57) ABSTRACT

A new and distinct *Aspidistra* cultivar named 'LEELASPIBL' is disclosed, characterized by leaves of ovate shape and pink, cream, and green color. The new variety is an *Aspidistra,* typically produced as an indoor ornamental plant.

1 Drawing Sheet

Latin name of the genus and species: *Aspidistra elatior.*
Variety denomination: 'LEELASPIBL'.

BACKGROUND OF THE INVENTION

The new cultivar is the product of chance discovery. The new variety originated as a naturally occurring whole plant mutation of an unpatented, unnamed variety of *Aspidistra elatior.*

The new variety was first selected by the inventor, Anon Leelachaikul, a citizen of Thailand, in January of 2004 at a nursery in Bangkok, Thailand. After identifying the new variety as a potentially interesting selection, the inventor continued confidential testing and propagation of 'LEELASPIBL', assessing stability of the unique characteristics of this variety.

Asexual reproduction of the new cultivar 'LEELASPIBL' by was first performed at the same nursery in Bangkok, Thailand during October of 2004. Vegetative propagation is by side shoots of the mother plants, which emerge from the roots. Subsequently many generations have been produced by this vegetative propagation method, and have shown that the unique features of this cultivar are stable and reproduced true to type.

SUMMARY OF THE INVENTION

The cultivar 'LEELASPIBL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LEELASPIBL'. These characteristics in combination distinguish 'LEELASPIBL' as a new and distinct *Aspidistra* cultivar:

1. Distinctive yellow-green and white spots on the foliage.
2. Light petiole coloration
3. Dark green background color of foliage.

PARENT COMPARISON

Plants of the new cultivar 'LEELASPIBL' are similar to the parent variety in most horticultural characteristics. The new cultivar, however, produces leaves that are have a darker green background coloration than those of the parent. Additionally the new cultivar produces a leaf with distinctive yellow speckling, whereas the parent variety has a solid green leaf. The petiole coloration of the new variety is lighter than petioles of the parent variety.

COMMERCIAL COMPARISON

Plants of the new cultivar 'LEELASPIBL' are comparable to the unpatented variety *Aspidistra* 'Milky Way'. The two *Aspidistra* varieties are similar in most horticultural characteristics; however, the new cultivar 'LEELASPIBL' differs in the following characteristics:

1. Leaves of 'LEELASPIBL' are lighter green than leaves of 'Milky Way'.
2. Leaves of 'LEELASPIBL' have more spots than leaves of 'Milky Way'.
3. The color of the spots of 'LEELASPIBL' are yellow and white, spots of 'Milky Way' are only white.
4. Leaves of 'LEELASPIBL' are strongly ribbed, a characteristic not found on foliage of 'Milky Way'.

BRIEF DESCRIPTION OF THE PHOTOGRAPH

The accompanying photograph in FIG. 1 illustrates in full color a typical plant of 'LEELASPIBL' grown in a commercial greenhouse in Rijswiijk, The Netherlands. This plant is approximately 2 months old shown planted in 15 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'LEELASPIBL' plants grown according to the following protocols.

Plants were grown in Rijswiijk, the Netherlands under controlled greenhouse conditions, with a temperature of 20° C. during the day and at night and with natural sunlight. Measurements and numerical values below represent averages of typical plant types.

Botanical classification: *Aspidistra elatior* 'LEELASPIBL'.

PROPAGATION

Time to initiate roots: About 14 days at approximately 20° C.

Root description: Moderately thick, very slightly fleshy, fibrous, moderately branched, colored yellow-white and greyed-green; near RHS 158A and 194A and 194B.

Time to produce rooted plantlet: Approximately 6-8 weeks at approximately 20° C.

PLANT

Growth habit: Leaves grow directly from rhizomes, no lateral branches/stems present.

Plant shape: Broad fan-shaped

Height: Approximately 39.0 cm to top of highest leaf.

Plant spread: Approximately 57.5 cm in a 15 cm pot.

Normal pot size: 1.5 liter (15 cm diameter) circular pot.

Growth rate: Moderate.

Stem: Leaves grow directly from rhizomes, no (lateral) stems present.

Number of leaves per plant: Approximately 11.

Age of plant described: Approximately 2 months.

FOLIAGE

Leaf:

*Arrangement.*—Alternate; leaves grow directly from rhizomes (randomly).

*Average length (excluding petiole).*—Approximately 32.7 cm.

*Average width.*—Approximately 7.0 cm.

*Shape of blade.*—Narrow elliptic.

*Aspect.*—Leaves at an average angle of 60° to completely horizontal.

*Apex.*—Acute to slightly acuminate.

*Base.*—Long acuminate.

*Margin.*—Entire.

*Texture of top surface.*—Smooth, with prominent venation. Ribbed.

*Texture of bottom surface.*—Smooth.

*Appearance.*—Slightly glossy top and bottom surfaces.

*Color.*—Young foliage upper side: Green; near RHS 143A, irregularly dotted yellow-green; near RHS 150C. Young foliage under side: Green; a color in between RHS 138A and 143A, irregularly dotted yellow-green; near RHS 150B. Mature foliage upper side: Green; near RHS N137B, irregularly dotted white; near RHS 155C and yellow-green; near RHS 150D. Mature foliage under side: Green; near RHS 137A, irregularly dotted yellow-green 150D and white 155D.

Venation:

*Type.*—Camptodrome.

*Venation coloration upper side.*—Main vein green; near 143A, other veins as leaf blade, green; near RHS N137B.

*Venation coloration under side.*—Main vein yellow-green; near 144A, other veins same color as leaf blade, green 137A.

Sheath:

*Average length.*—Approximately 6.8 cm.

*Average width.*—Approximately 2.3 cm unfolded.

*Color.*—Under side (outside) greyed-purple to black; in between RHS N186A and 203A, lighter towards the margin; near RHS N186C. Upper side (inside) yellow-green; near RHS 147B, tinged greyed-purple; near RHS 187A.

*Texture.*—Both sides smooth, under (outer) side moderately glossy in apperance, upper (inner) side very slightly glossy in appearance.

*Other distinguishing characteristics.*—No.

Petiole (excluding geniculum):

*Length.*—Approximately 11.2 cm.

*Width.*—At geniculum: Approximately 0.4 cm. Above clump: Approximately 0.5 cm.

*Color.*—Yellow-green; near RHS 144A.

*Strength.*—Strong.

Geniculum:

*Length.*—Approximately 1.4 cm.

*Width.*—Approximately 0.45 cm.

*Color.*—Yellow-green; near RHS 144A.

*Other characteristics.*—Geniculum very hard to see, only very slightly wider than petiole at distal end and of the same colour.

Any other foliar structures: No.

FLOWERING CHARACTERISTICS

Flowering not observed to date.

REPRODUCTIVE ORGANS

Not observed to date

OTHER CHARACTERISTICS

Disease resistance: Good resistance to the normal diseases found in *Aspidistra,* which are most commonly; *Fusarium* and *Sclerotium rolfsii.*

Drought tolerance and cold tolerance: Normal for species. USDA zone 10 and higher.

Fruit/seed production: No fruits/seeds detected to date.

What is claimed is:

1. A new and distinct cultivar of *Aspidistra* plant named 'LEELASPIBL' as herein illustrated and described.

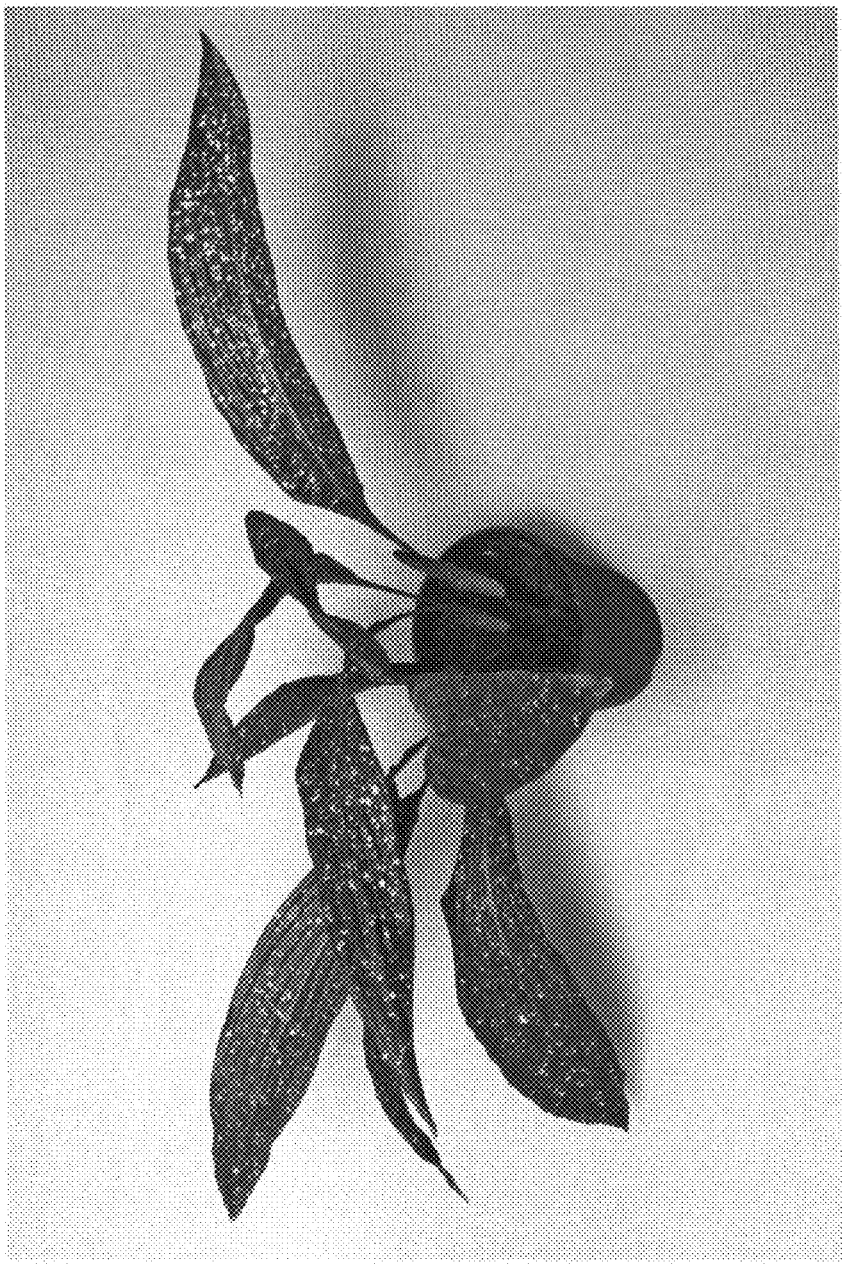

* * * * *